US012723258B2

(12) United States Patent
Chen et al.

(10) Patent No.: US 12,723,258 B2
(45) Date of Patent: Sep. 1, 2026

(54) **RESISTANCE GENE *TaCAT* TO *FUSARIUM* CROWN ROT OF WHEAT AND APPLICATION THEREOF**

(71) Applicant: Henan Agricultural University, Zhengzhou (CN)

(72) Inventors: Feng Chen, Zhengzhou (CN); Xia Yang, Zhengzhou (CN); Dan Pei, Zhengzhou (CN); Xiaodong Yu, Zhengzhou (CN); Yan Yan, Zhengzhou (CN); Yan Ren, Zhengzhou (CN); Ning Zhang, Zhengzhou (CN); Lei Zhao, Zhengzhou (CN)

(73) Assignee: HENAN AGRICULTURAL UNIVERSITY, Zhengzhou (CN)

( * ) Notice: Subject to any disclaimer, the term of this patent is extended or adjusted under 35 U.S.C. 154(b) by 106 days.

(21) Appl. No.: 18/827,889

(22) Filed: Sep. 9, 2024

(65) Prior Publication Data

US 2025/0163451 A1 May 22, 2025

(30) Foreign Application Priority Data

Nov. 20, 2023 (CN) ......................... 202311547240.9

(51) Int. Cl.
*C12N 15/82* (2006.01)
*A01H 1/04* (2006.01)
*C12Q 1/6895* (2018.01)

(52) U.S. Cl.
CPC ....... *C12N 15/8282* (2013.01); *C12Q 1/6895* (2013.01); *A01H 1/045* (2021.01); *C12Q 2600/13* (2013.01); *C12Q 2600/156* (2013.01)

(58) Field of Classification Search
CPC .......................... C12N 15/8282; C12Q 1/6858
See application file for complete search history.

(56) References Cited

U.S. PATENT DOCUMENTS 9,115,368 B2 * 8/2015 Abad ............. C12Y 102/01024

OTHER PUBLICATIONS

Sun, T., et al. The Role of Sugarcane Catalase Gene ScCAT2 in the Defense Response to Pathogen Challenge and Adversity Stress.Int. J. Mol. Sci. 2018, 19, 2686. https://doi.org/10.3390/ijms19092686, published Sep. 9, 2018 (Year: 2018).*
NCBI Genbank accession XP_044407354.1 (catalase isozyme 2-like [Triticum aestivum], published Oct. 25, 2021) (Year: 2021).*
Zhang (Zhang, Y, et al. Catalase (CAT) Gene Family in Wheat (*Triticum aestivum* L.): Evolution, Expression Pattern and Function Analysis. Int J Mol Sci. Jan. 4, 2022;23(1):542. doi: 10.3390/ijms23010542. PMID: 35008967; PMCID: PMC8745605., published Jan. 4, 2022) (Year: 2022).*
McKnight T, Hart J, Some field observations on crown rot disease of wheat caused by Fusarium graminearum, Queensland Journal of Agricultural and Animal Sciences, 1966, 23:373-378.
Yang et al., Investigation and genome-wide association study for Fusarium crown rot resistance in Chinese common wheat, BMC Plant Biology, Apr. 23, 2019, 19: 153.
Yang et al., A loss-of-function of the dirigent gene TaDIR-B1 improves resistance to Fusarium crown rot in wheat, Plant Biotechnology Journal, May 2021, 19: 866-868.
Wang et al., Horizontal gene transfer of Fhb7 from fungus underlies Fusarium head blight resistance in wheat, Science, Apr. 9, 2020, 368:5435.
Lv et al., A cell wall invertase modulates resistance to fusarium crown rot and sharp eyespot in common wheat, Journal of Integrative Plant Biology, Jul. 2023, 65:1814-1825.
Sun et al., The Wheat 660K SNP array demonstrates great potential for marker-assisted selection in polyploid wheat, Plant Biotechnology Journal, Jun. 2020, 18:1354-1360.

* cited by examiner

*Primary Examiner* — Bratislav Stankovic
*Assistant Examiner* — Yvette Bih Tamukong

(57) ABSTRACT

A resistance gene TaCAT to FCR of wheat and an application thereof are provided, which relates to the field of biological genetic engineering technologies. The nucleotide sequence of a genome where the TaCAT gene is located, the nucleotide sequence of a cDNA, the nucleotide sequence of a CDS and a coded protein sequence are respectively as shown in SEQ ID NO: 1, SEQ ID NO: 2, SEQ ID NO: 3 and SEQ ID NO: 4. An InDel marker is developed for identifying different allelotypes of the TaCAT gene. An application of the TaCAT gene for preparation of transgenic plant cells and plant breeding is provided. The molecular genetic basis of the resistance to FCR is disclosed, an important role is played in improving the resistance to FCR by utilizing a genetic engineering technology, and a new way is provided for breeding a new wheat variety with disease-resistance and safety.

2 Claims, 11 Drawing Sheets

Specification includes a Sequence Listing.

| *Haplotype* | 215 bp-InDel | +1007 | +1618 | Numbers | Types |
|---|---|---|---|---|---|
| *HapA* | - | TT | GG | 46 | *TaCAT-R* |
| *HapB* | - | TT | AA | 13 | *TaCAT-M* |
| *HapC* | + | TT | GG | 8 | |
| *HapD* | + | TT | AA | 5 | |
| *HapE* | - | AA | GG | 8 | |
| *HapF* | - | AA | AA | 5 | |
| *HapG* | + | AA | GG | 2 | |
| *HapH* | + | AA | AA | 97 | *TaCAT-S* |

RESISTANCE GENE *TaCAT* TO *FUSARIUM* CROWN ROT OF WHEAT AND APPLICATION THEREOF

CROSS-REFERENCE TO RELATED APPLICATION

This application claims priority to Chinese Patent Application No. 202311547240.9, filed on Nov. 20, 2023, which is herein incorporated by reference in its entirety.

TECHNICAL FIELD

The disclosure relates to the field of biological genetic engineering technologies, and more particularly to a resistance gene TaCAT to *Fusarium* crown rot of wheat and an application thereof.

STATEMENT REGARDING SEQUENCE LISTING

The sequence listing associated with this application is provided in text format in lieu of a paper copy and is hereby incorporated by reference into the specification. The name of the XML file containing the sequence listing is 24086TBYX-USP1-SL-R.xml. The XML file is 21,516 bytes; is created on Mar. 27, 2026; and is being submitted electronically via patent center.

BACKGROUND

*Fusarium* crown rot (FCR) of wheat is a typical soil-borne disease, which was first reported for similar symptoms in Australia in 1940 by Mcknight et al (McKnight T, Hart J, Some field observations on crown rot disease of wheat caused by *Fusarium graminearum*, Queensland Journal of Agricultural and Animal Sciences, 1966, 23:373-378). At present, the FCR of wheat has spread to become a global disease, which is widely distributed around the world, including North America, South America, Europe, Africa, Mediterranean coastal countries, most Asian countries, New Zealand and Australia in Oceania, etc. In China, the FCR of wheat caused by *Fusarium pseudograminearum* was first reported in 2012.

The FCR of wheat not only causes serious yield and economic losses during its occurrence, but also produces multiple toxins and secondary metabolites, such as nivalenol (NIV), deoxynivalenol (DON) and zearalenone (ZEN) (Yang et al., Investigation and genome-wide association study for *Fusarium* crown rot resistance in Chinese common wheat, BMC Plant Biology, Apr. 23, 2019, 19: 153). On the one hand, these substances can be pathogenic factors of pathogens to damage plants, on the other hand, these substances can contaminate host plants and affect the safety of plant products, processed foods and feeds. NIV and DON are potential carcinogens, which can cause serious harm to health of human and livestock.

Due to scarcity of disease-resistant resources and narrow genetic background of current varieties, a wheat variety with immunity or high resistance to the FCR has not yet been identified. At present, researches on the FCR of wheat are mostly focused on collection of pathogens, identification of material resistance and preliminary mapping of genes. Up to now, almost all 21 chromosomes of hexaploid wheat have been reported to contain quantitative trait loci (QTL) for resistance to the FCR, and the QTL that can be repeatedly detected are located on chromosomes 2DL, 3BL, 4BS and 5DS, but these QTL often contain only partial resistance or unstable resistance (Yang et al., A loss-of-function of the dirigent gene TaDIR-B1 improves resistance to *Fusarium* crown rot in wheat, Plant Biotechnology Journal, May 2021, 19: 866-868). In addition, the reported genes related to resistance to the FCR of wheat include Fhb7 (Wang et al., Horizontal gene transfer of Fhb7 from fungus underlies *Fusarium* head blight resistance in wheat, Science, Apr. 9, 2020, 368:5435), TaDIR-4B (Yang et al., A loss-of-function of the dirigent gene TaDIR-B1 improves resistance to *Fusarium* crown rot in wheat, Plant Biotechnology Journal, May 2021, 19:866-868) and TaCWI-B1 (Lv et al., A cell wall invertase modulates resistance to *fusarium* crown rot and sharp eyespot in common wheat, Journal of Integrative Plant Biology, July 2023, 65:1814-1825). These genes play an important role in resistance of wheat to the FCR infection, but the effect size and stability of the genes need to be further verified.

Due to a lack of recognized identification standards for the FCR of wheat, generally poor resistance of wheat varieties, and significant genetic background limitations, the discovery and development of resistance genes to the FCR of wheat has been slow. Therefore, expanding a scope of germplasm resource screening, discovering and utilizing excellent disease-resistant genes, and exploring regulatory pathways involved in the disease-resistant genes are of great significance to aggregation and utilization of the resistance genes to the FCR of wheat.

SUMMARY

A purpose of the disclosure is to provide a resistance gene TaCAT to FCR of wheat and an expression product thereof, as well as primers, a silencing vector and a plant expression vector for detecting genotypes of the FCR of wheat, and to apply the resistance gene TaCAT to the FCR of wheat and the expression product thereof, as well as the primers, the silencing vector and the plant expression vector to prevention and breeding of the FCR of wheat, to thereby provide more selections for breeding for resistance to the FCR of wheat.

In order to solve the above technical problems, the disclosure adopts the following technical solutions.

1. The disclosure provides a TaCAT gene related to the FCR of wheat, the nucleotide sequence of a genome where the TaCAT gene is located is as shown in SEQ ID NO: 1, the nucleotide sequence of a full-length complementary deoxyribonucleic acid (cDNA) of the TaCAT gene is as shown in SEQ ID NO: 2, and the nucleotide sequence of a coding sequence (CDS) of the TaCAT gene is as shown in SEQ ID NO: 3.

2. The disclosure provides a protein coded by the TaCAT gene related to the FCR of wheat, and the amino acid sequence of the protein coded by the TaCAT gene is as shown in SEQ ID NO: 4.

3. The disclosure further provides a specific primer pair for detecting the TaCAT gene related to the FCR of wheat, and the specific primer pair includes: an upstream primer with the nucleotide sequence as shown in SEQ ID NO: 5, and a downstream primer with the nucleotide sequence as shown in SEQ ID NO: 6.

A method for detecting an allelotype of the FCR of wheat by using the above specific primer pair includes:

step 1, extracting genomic DNA of a to-be-detected wheat; and step 2, taking the genomic DNA of the to-be-detected wheat as a template, performing a polymerase chain reaction (PCR) amplification with the upstream primer with the nucleotide sequence as shown in SEQ ID NO: 5, and the downstream primer with the nucleotide sequence as shown in SEQ ID NO: 6, to obtain an amplification product as shown in SEQ ID NO: 1, and detecting the allelotype of the *Fusarium* crown rot of wheat based on the amplification product as shown in SEQ ID NO: 1; and where a resistant and susceptible material has an insertion or deletion (InDel) of 215 base pairs (bp) starting from a $654^{th}$ position after a start codon adenine-thymine-guanine (ATG) in the gene sequence as shown in SEQ ID NO: 1, and a genotype of the amplification product is determined according to the InDel; and a genotype corresponding to an insertion type amplification product is named as TaCAT-6Aa, and a genotype corresponding to a deletion type amplification product is named as TaCAT-6Ab.

The phenotype identification results show that a plant corresponding to the genotype of TaCAT-6Aa is severely affected and has a high disease index, and resistance of the plant corresponding to the genotype of TaCAT-6Aa to the FCR of wheat is lower than resistance of a plant corresponding to the genotype of TaCAT-6Ab to the FCR of wheat. The plant corresponding to the genotype of TaCAT-6Ab has mild disease incidence and a low disease index, and the resistance of the plant corresponding to the genotype of TaCAT-6Ab to the FCR of wheat is higher than the resistance of the plant corresponding to the genotype of TaCAT-6Aa to the FCR of wheat. Therefore, the TaCAT gene plays a crucial role in the resistance to the FCR of wheat.

Alternatively, in step 2, an InDel marker is developed according to the insertion or deletion fragment to detect different genotypes of the TaCAT gene. A differential site-specific primer pair includes: an upstream primer with the nucleotide sequence as shown in SEQ ID NO: 7, and a downstream primer with the nucleotide sequence as shown in SEQ ID NO: 8.

The specific InDel marker is used to amplify DNA from different materials. A genotype of a wheat variety/strain with an amplification product of 1054 bp is named as TaCAT-6Aa, a genotype of a wheat variety/strain with an amplification product of 839 bp is named as TaCAT-6Ab (FIG. 4A), and there is a significant difference in the disease resistance ability of plants corresponding to the two genotypes.

4. The disclosure further designs a virus-induced gene silencing (VIGS) vector of the TaCAT gene.

Primer sequences for amplifying a silencing fragment include: an upstream primer with the nucleotide sequence as shown in SEQ ID NO: 9, and a downstream primer with the nucleotide sequence as shown in SEQ ID NO: 10. The silencing fragment of PCR amplification can be seamlessly cloned and connected between restriction enzyme cutting sites PacI and NotI of a γ-PDS-as vector to obtain a recombinant plasmid.

The recombinant plasmid is further linearized and transcribed in vitro to obtain RNA virus, which is inoculated into wheat seedling leaves to silence the TaCAT gene (a blank control and a whitening positive control are set up), to thereby verify the function of the TaCAT gene.

5. The disclosure further designs a plant expression vector containing the TaCAT gene, and the above recombinant vector (i.e., the recombinant plasmid) can be used to construct recombinant bacteria.

The plant expression vector used is specifically a binary *Agrobacterium* vector or a plant microprojectile bombardment vector, and the recombinant vector is obtained by inserting the nucleic acid sequence as shown in SEQ ID NO: 3 between restriction enzyme cutting sites of the plant expression vector.

The plant expression vector can also include a 3'-untranslated region of a foreign gene (also referred to as exogenous gene), that is, the plant expression vector includes a polyadenylic acid signal and other DNA fragments involved in mRNA processing or gene expression. The polyadenylic acid signal can guide addition of polyadenylic acid to a 3' end of a mRNA precursor. For example, the *Agrobacterium tumefaciens* induction (tumor-inducing abbreviated as Ti) plasmid gene and the untranslated region transcribed at the 3' end of the plant gene (such as soybean storage protein gene) have a similar function. When the gene is used to construct a recombinant plant expression vector, any enhanced promoter or constitutive promoter can be added before transcribing a start nucleotide, and the enhanced promoter or the constitutive promoter can be used alone or in combination with other plant promoters. In addition, when the gene of the disclosure is used to construct the plant expression vector, an enhancer can also be used, and the enhancer includes a transcription enhancer or a translation enhancer. The enhancer regions can be ATG start codons or start codons in adjacent regions, but must be the same as a reading frame of the coding sequence to ensure a correct translation of the entire sequence. In order to facilitate the identification and screening of transgenic plant cells or transgenic plants, the plant expression vector used can be processed and modified, such as adding enzymes or luminescent groups (luciferase gene, β-glucuronidase abbreviated as GUS gene, etc.) that can produce color changes through coding, antibiotic markers (kanamycin markers, gentamicin markers, etc.) with resistance, or chemical agent resistance marker genes (herbicide resistance genes, etc.) that can be expressed in plants. For considering the safety of the transgenic plants, no selective marker genes can be added, and transformed plants can be directly screened with appropriate disease pressure.

The disclosure further provides an application method of the TaCAT gene, including: breeding a wheat variety resistant to the FCR by using the TaCAT gene. That is, the TaCAT gene is transformed into a target plant to obtain a transgenic plant for adjusting resistance to the FCR. The expression vector carrying the TaCAT gene can transform plant cells or tissues by using conventional biological methods such as Ti plasmid, rhizobium-inducible (Ri) plasmid (also referred to root-inducing plasmid), plant virus vector, DNA transformation, microinjection, electroporation, *Agrobacterium*-mediated transformation, gene gun, etc., and the transformed plant tissues are cultivated into a plant for subsequent research.

The target plant can be either a monocot or a dicot. The monocot can be wheat, such as Kenong 199 (KN199, cultivated by Institute of Genetics and Developmental Biology, Chinese Academy of Sciences in 2006, approval number: national approved wheat variety 2006017).

Compared to the related art, main beneficial technical effects of the disclosure are as follows.

1. The disclosure has identified a new gene related to the FCR of wheat, which is named TaCAT, the gene is located on a chromosome 6A of the wheat and the protein expressed by the gene can regulate resistance of wheat to the FCR.

2. The disclosure clarifies the DNA sequence, CDS sequence and the coded protein sequence of the TaCAT gene related to the FCR of wheat, which lays a technical foundation for application practice of breeding a wheat variety resistant to the FCR in the future.

3. The specific primers in the disclosure can be directly used for the detection of different alleles of the FCR of wheat, which is beneficial to the screening and breeding of a disease-resistant wheat variety and can effectively save time and resources.

4. The disclosure uses the VIGS technology to silence the TaCAT gene related to the FCR of wheat, to thereby verify a role of the TaCAT gene in breeding the wheat variety resistant to the FCR.

5. The disclosure uses the transgenic technology to transform the resistance gene TaCAT to the FCR of wheat into a common wheat for overexpression for the first time, to thereby verify the role of the TaCAT gene in breeding the wheat variety resistant to the FCR.

6. The disclosure helps to reveal a molecular genetic basis of the FCR of wheat. Meanwhile, the disclosure plays an important role in detecting and improving wheat varieties by using a genetic engineering technology, and provides a new way to breed disease-resistant and safe new wheat varieties.

DETAILED DESCRIPTION OF EMBODIMENTS

Figure 1:
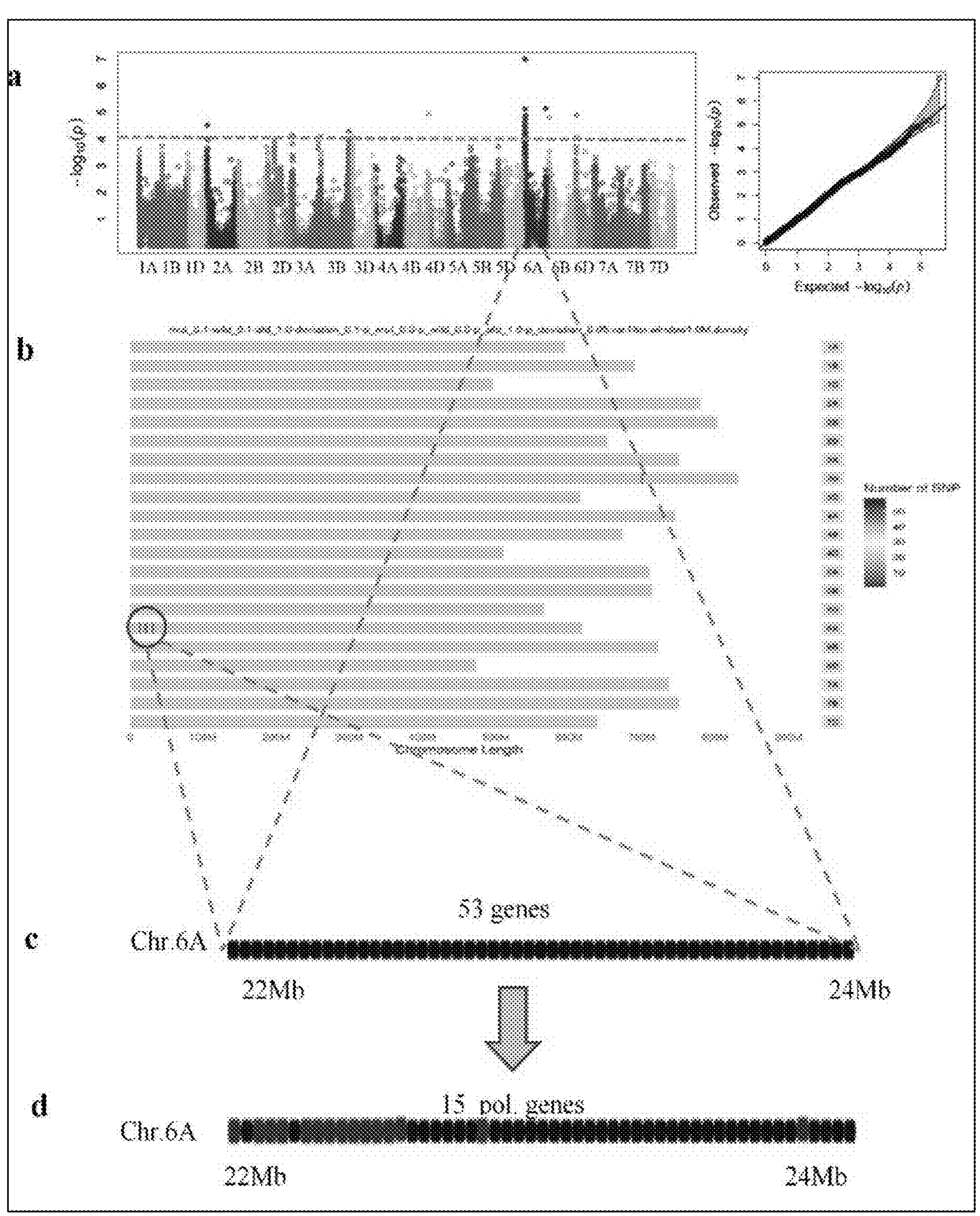
FIG. 1 illustrates a schematic diagram of a genome-wide association study (GWAS) combined with a whole exome sequencing (WES) to locate resistance regions. Specifically, a represents the GWAS; b represents the WES; c represents a co-located segment; and d represents polymorphic gene within the co-located segment.

The disclosure is described in more detail below through embodiments, to facilitate understanding of technical solutions of the disclosure, but is not intended to limit a scope of protection of the disclosure.

Unless otherwise specified, instruments and equipment involved in the following embodiments are all conventional instruments and equipment. Phenotypic identification experiments in the following embodiments are set up for three repeated experiments, and results are averaged. Primer synthesis and sequencing are completed by Sangon Biotech (Shanghai) Co., Ltd.

The involved wheat materials include: a natural population consisting of 243 main varieties promoted in the Huanghuai wheat region in recent years (Table 1), two $F_4$ generation recombinant inbred lines (RIL) populations (including a JY population and a JZ population), Jinmai 1 (JM1, cultivated by Shanxi Sanyuan Golden Seed Zhongye Technology Co., Ltd. and Xianyang Agricultural Science Research Institute cultivateShaanxi Sanyuan Golden Seed Zhongye Technology Co., Ltd. and Xianyang Agricultural Science Research Institute, approval number: Shanxi approved wheat variety: 2014006), a Kronos mutant (mutated by Jorge Dubcovsky, gene ID: TraesCS6A02G041700.1) and KN199.

A wheat 660 kilo (K) single nucleotide polymorphism (SNP) array (Sun et al., The Wheat 660K SNP array demonstrates great potential for marker-assisted selection in polyploid wheat, Plant Biotechnology Journal, June 2020, 18:1354-1360) covering a whole genome is used for genotyping on the natural population, and the natural population is used for GWAS.

The two $F_4$ generation RIL populations are constructed by hybridizing a disease-resistant variety JM1 with susceptible varieties Yunong 805 (YN805, cultivated by Henan agricultural university, approval number: Henan approved wheat variety: 20180023) and Zhengmai 082 (ZM082, cultivated by Henan Academy of Agricultural Sciences, approval number: Henan approved wheat variety 20220055), respectively.

The two $F_4$ generation RIL populations are used for WES, bulking transcriptome sequencing, and bulking proteome sequencing.

The JM1 has genotype and phenotype resistant to FCR of wheat, and used for a VIGS experiment to verify a disease-resistance effect of a TaCAT gene;

The Kronos mutant includes a wild-type Kronos-WT and Kronos3868 (the TaCAT gene premature termination mutant), and used to verify the disease resistance effect of the TaCAT gene.

The KN199 is a susceptible variety for the FCR of wheat, and is used as an overexpression transgenic receptor material to verify the disease-resistance function of the TaCAT gene.

TABLE 1

Details of population materials used for GWAS

| Number | Name | Number | Name | Number | Name | Number | Name |
|---|---|---|---|---|---|---|---|
| 1 | Tianning 18 (TN18) | 2 | Zhongxin 18 (ZX18) | 3 | Jiamai 99 (JM99) | 4 | Keyu 368 (KY368) |
| 5 | Zongmai 108 (ZM108) | 6 | Bainong 1309 (BN1309) | 7 | Hemai 181 (HM181) | 8 | Taixue 30 (TX30) |
| 9 | Qunximai (QXM11) | 1110 | Fengtian 18 (FT18) | 11 | Heyu 1 (HY1) | 12 | Shengmai 102 (SM102) |
| 13 | Xinmai 68 (XM68) | 14 | Zhengmai 1869 (ZM1869) | 15 | Hongmai 618 (HM618) | 16 | Fengdecunmai 20 (FDCM20) |
| 17 | Xinyoumai 2 (XYM2) | 18 | Jiamai 6 (JM6) | 19 | Fanmai 533 (FM533) | 20 | Zhengmai 518 (ZM518) |
| 21 | Xingnong 168 (XN168) | 22 | Yanmai 9719 (YM9719) | 23 | Luo 1807 (L1807) | 24 | Yanfeng 712 (YF712) |
| 25 | Zimai 627 (ZM627) | 26 | Yunong 805 (YN805) | 27 | Zhengxin 758 (ZX758) | 28 | Gengmai 256 (GM256) |
| 29 | Yanke 316 (YK316) | 30 | Fumai 188 (FM188) | 31 | Lunxuan 162 (LX162) | 32 | Jingjiumai 11 (JJM11) |
| 33 | Yunong 804 (YN804) | 34 | Gengmai 237 (GM237) | 35 | Jinmai 1 (JM1) | 36 | Liming 28 (LM28) |
| 37 | Qinmai 158 (QM158) | 38 | Junmai 118 (JM118) | 39 | Caiyuan 1 (CY1) | 40 | Junhe 183 (JH183) |
| 41 | Ximai 505 (XM505) | 42 | Kaimai 26 (KM26) | 43 | Zhoukang 918 (ZK918) | 44 | Zhengnong 06118 (ZN06118) |
| 45 | Nongda 399 (ND399) | 46 | Zhongying 012 (ZY012) | 47 | Zhouyumai 36 (ZYM36) | 48 | Jinying 18 (JY18) |
| 49 | Zhengmai 082 (ZM082) | 50 | Zhengmai 516 (ZM516) | 51 | Xuke 877 (XK877) | 52 | Zhongkenmai 7 (ZKM7) |
| 53 | Chuangxing 6 (CX6) | 54 | Luyuan 502 (LY502) | 55 | Zhongfengmai (ZFM2) | 256 | Hengmai 18 (HM18) |
| 57 | Neimai (NM6) | 658 | Fengbao 8 (FB8) | 59 | Tianle 6 (TL6) | 60 | Xinmai 37 (XM37) |
| 61 | Hemai (HM6) | 662 | Junmai 667 JM667) | 63 | Nongfeng 11164 (NF111) | | Wenliang 1 (WL1) |
| 65 | Pingan 0602 (PA0602) | 66 | Huayu 3568 (HY3568) | 67 | Guangtai 369 (GT369) | 68 | Yunong 169 (YN169) |
| 69 | Zhonglemai (ZLM9) | 970 | Jinsui 8 (JS8) | 71 | Jingkemai 6 (JKM6) | 72 | Xinxuan 17 (XX17) |
| 73 | TH161 | 74 | Jinmai 108 (JM108) | 75 | Jinyan 5 (JY5) | 76 | Huayu 126 (HY126) |
| 77 | Baiqiang 1201 (BQ121) | 78 | Yimai 8 (YM8) | 79 | Hefeng 3 (HF3) | 80 | Lunxuan 163 (LX163) |
| 81 | Yunong 019 (YN019) | 82 | Zhongle 8 (ZL8) | 83 | Ruisen 218 (RS218) | 84 | Fanning 3 (FN3) |
| 85 | Hemai 2 (HM2) | 86 | Xuke 732 (XK732) | 87 | Jinmai 14 (JM14) | 88 | Haozhuangjia 1 (HZJ1) |
| 89 | Xuyou 46 (XY46) | 90 | Hanmai 457 (HM457) | 91 | Fengdecunmai 19 (FDCM19) | 192 | Hangmai 8 (HM8) |
| 93 | L668 | 94 | Qiangmai 29 (QM29) | 95 | Luyan 260 (LY260) | 96 | Yanhao 306 (YH306) |
| 97 | Caizhi 204 (CZ204) | 98 | Zhengpinmai 24 (ZPM24) | 99 | Luomai 2 (LM2) | 100 | Anyumai 18 (AYM18) |
| 101 | Wenyu 019 (WY019) | 102 | Taipingyuan 18 (TPY18) | 103 | Jingyumai 1 (JYM1) | 104 | Luomai 718 (LM718) |
| 105 | Yanmai 26 (YM26) | 106 | Junmai 188 (JM188) | 107 | Tianmai 119 (TM119) | 108 | Fengmai 53 (FM53) |
| 109 | Danmai 108 (DM108) | 110 | Xinmai 38 (XM38) | 111 | Changshengmai 1 (CSM1) | 112 | Defeng 108 (DF108) |
| 113 | Shaomai 25 (SM25) | 114 | Tongfeng 736 (TF736) | 115 | Meng 615 (M615) | 116 | Boyu 866 (BY866) |
| 117 | Bainong 1306 (BN1306) | 118 | Jiamai 8 (JM8) | 119 | Xianhong 169 (XH169) | 120 | Yanmai 888 (YM888) |
| 121 | Shengyuan 928 (SY928) | 122 | Jun 5366 (J5366) | 123 | Zhengnong 5222 (ZN5222) | 124 | Xuke 682 (XK682) |
| 125 | Xinzhi 519 | 126 | Xuyan 2 (XY2) | 127 | Hangmai 6 | 128 | Yunong 1235 |

TABLE 1-continued

| Details of population materials used for GWAS | | | | | | | |
|---|---|---|---|---|---|---|---|
| Number | Name | Number | Name | Number | Name | Number | Name |
| | (XZ519) | | | | (HM6) | | (YN1235) |
| 129 | Fanmai 536 (FM536) | 130 | Yufeng 1366 (YF1366) | 131 | Xinmai 12 (XM12) | 132 | Xunong 618 (XN618) |
| 133 | Ningnong 718 (NN718) | 134 | Yuyan 168 (YY168) | 135 | Shunmai 8 (SM8) | 136 | Aomai 18 (AM18) |
| 137 | Pumai 27 (PM27) | 138 | Tianlaoda 3 (TLD3) | 139 | Xingyu 7 (XY7) | 140 | Xinong 18 (XN18) |
| 141 | Yongfengnong 2 (YFN2) | 142 | Guangtai 213 (GT213) | 143 | Qiule 2126 (QL2126) | 144 | Nongfeng 8210 (NF8210) |
| 145 | Saidemai 7 (SDM7) | 146 | Dongfanghongmai 6 (DFH6) | 147 | Jinmai 18 (JM18) | 148 | Jimai 210 (JM210) |
| 149 | Kaimai 27 (KM27) | 150 | Jinmai 109 (JM109) | 151 | Hengda 58 (HD58) | 152 | Maifeng 9 (MF9) |
| 153 | Jinchengmai 10 (JCM10) | 154 | Xianmai 15 (XM15) | 155 | Yanmai 988 (YM988) | 156 | Xianyuan 988 (XY988) |
| 157 | Lunxuan 169 (LX169) | 158 | Xinmai 8 (XM8) | 159 | Wenmai 29 (WM29) | 160 | Wenyuan 0528 (WY0528) |
| 161 | Jinwoye 1 (JWY1) | 162 | Changmai 13 (CM13) | 163 | Kun 169 (K169) | 164 | SM110 |
| 165 | Bainong 219 (BN219) | 166 | Sanhe 1 (SH1) | 167 | Xiza 5 (XZ5) | 168 | Yufeng 6 (YF6) |
| 169 | Taipingyuan 007 (TPY007) | 170 | Songmai 518 (SM518) | 171 | Shenzhou 209 (SZ209) | 172 | Yunong 99 (YN99) |
| 173 | Shangmai 162 (SM162) | 174 | Junmai 612 (JM612) | 175 | Jiyanmai 10 (JYM10) | 176 | Aifeng 338 (AF338) |
| 177 | Liangmai 958 (LM958) | 178 | Fengmai 52 (FM52) | 179 | Chuangmai 11 (CM11) | 180 | Wanmai 99 (WM99) |
| 181 | Xinhuamai 818 (XHM818) | 182 | Zhumai 706 (ZM706) | 183 | Taifeng 11 (TF11) | 184 | Luomai 32 (LM32) |
| 185 | Zhongmai 10 (ZM10) | 186 | Jinchengmai 12 (JCM12) | 187 | Chuangxin 106 (CX106) | 188 | Huaichuan 361 (HC361) |
| 189 | Xianmai 522 (XM522) | 190 | Jinfeng 216 (JF216) | 191 | Jinzhan 638 (JZ638) | 192 | Xiangmai 1123 (XM1123) |
| 193 | Lunxuan 167 (LX167) | 194 | Xuke 158 (XK158) | 195 | Chuangxin 116 (CX116) | 196 | Zhengda 101 (ZD101) |
| 197 | Jiamai 329 (JM329) | 198 | Luomai 166 (LM166) | 199 | Fanning 1 (FN1) | 200 | Kelinmai 969 (KLM969) |
| 201 | Bomai 118 (BM118) | 202 | Wohua 066 (WH066) | 203 | Minfeng 296 (MF296) | 204 | Zimai 615 (ZM615) |
| 205 | Xuanmai 6 (XM6) | 206 | Weimin 208 (WM208) | 207 | Yingmai 182 (YM182) | 208 | Shenhua 208 (SH208) |
| 209 | Jumai 66 (JM66) | 210 | Yufeng 2 (YF2) | 211 | Yanmai 68 (YM68) | 212 | Yumai 117 (YM117) |
| 213 | Liangyuan A6 (LYA6) | 214 | Mengnong 1 (MN1) | 215 | Zhenmai 5 (ZM5) | 216 | Xinxuan 16 (XX16) |
| 217 | Lifu 05 (LF05) | 218 | Fanyumai 18 (FYM18) | 219 | Yingman 180 (YM180) | 220 | Xianmai 521 (XM521) |
| 221 | Jiangmai 816 (JM816) | 222 | Danmai 118 (DM118) | 223 | Tianmin 688 (TM688) | 224 | Shuanmai 299 (SM299) |
| 225 | Xuyan 3 (XY3) | 226 | Zhengda 3087 (ZD3087) | 227 | Zhaofeng 668 (ZF668) | 228 | Fengmai 10 (FM10) |
| 229 | Chuangxin 26 (CX26) | 230 | Yufeng 1 (YF1) | 231 | Neile 268 (NL268) | 232 | Pingnongyan 3 (PNY3) |
| 233 | Hongtaiyang 2 (HTY2) | 234 | Tianlaoda 1 (TLD1) | 235 | Xinyanmai 98 (XYM98) | 236 | Hongmai 186 (HM196) |
| 237 | Huayan (HY328) | 328238 | Huimai (HM216) | 216239 | Nongda 2018240 (ND2018) | | Jiyanmai 7 (JYM7) |
| 241 | Jinfeng 205 (JF205) | 242 | Taihemai 3 (THM3) | 243 | Zhengke 6 (ZK6) | | |

Figure 2A:
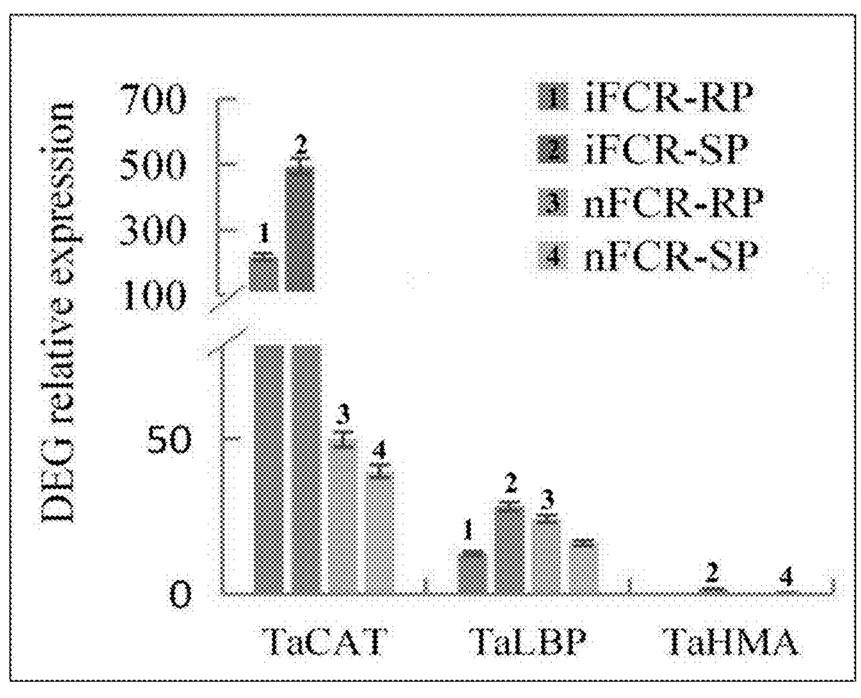
FIG. 2A illustrates a schematic diagram of differentially expressed genes within a localization segment excavated by a bulking transcriptome. Specifically, FCR-RP represents a material in a resistance pool to FCR; FCR-SP represents a material in a susceptible pool to the FCR; i represents a bacterial inoculation treatment; and n represents no bacterial inoculation treatment.
Figure 2B:
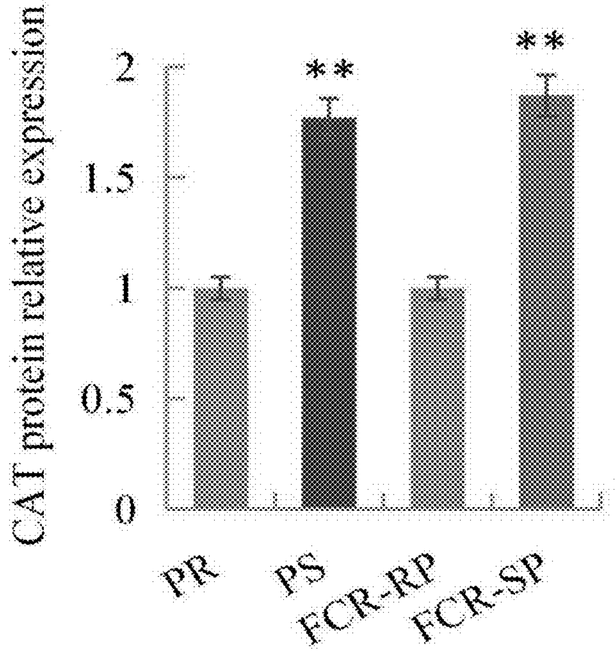
FIG. 2B illustrates a schematic diagram of differentially expressed proteins within a localization segment excavated by a bulking proteome. Specifically, PR represents a resistance parent; and PS represents a susceptible parent.

Embodiment 1 Mapping and Acquisition of the TaCAT Gene Related to the FCR of Wheat A millet medium inoculation method is used to identify resistance of the natural population consisting of 243 wheat varieties in the Huanghuai wheat region to the FCR, and GWAS is performed (part a in FIG. 1). The resistant and susceptible materials of the two $F_4$ generation populations (JY, JZ) are used for WES (part b in FIG. 1). A resistance segment is co-localized in 22 mega base pairs (Mb) to 24 Mb segment of a chromosome 6A of the wheat, which contains 53 annotated genes, of which the promoters or coding regions of 15 genes are different in the resistant and susceptible materials (FIG. 1). Based on the bulking transcriptome sequencing analysis of the JY population, 3 out of the 15 genes can be induced by the FCR, that is, TaCAT (TraesCS6A02G041700), TaLBP (TraesCS6A02G042600) and TaHMA (TraesCS6A02G043000). Specifically, an expression level of the TaCAT gene in each pool is significantly higher than that of TaLBP and TaHMA (FIG. 2A). Based on the bulking proteome sequencing analysis of the JY population, protein coded by the TaCAT gene can be detected in the above co-located segments, and difference of the expression level of the TaCAT gene between the parent pool and the descendant pool is significant (FIG. 2B). In summary, the TaCAT gene is related to the FCR of wheat.

A Primer 5 software is used to design primers to amplify the TaCAT gene. A forward primer of the primer pair is an upstream primer with the nucleotide sequence as shown in SEQ ID NO: 5, and a reverse primer of the primer pair is a downstream primer with the nucleotide sequence as shown in SEQ ID NO: 6.

The nucleotide sequences of the upstream primer and the downstream are as follows:

```
TaCAT-F1 as shown in SEQ ID NO: 5:
5'-AGAGAGCAGTGCAGTGAGAG-3';
and

TaCAT-R1 as shown in SEQ ID NO: 6:
5'-GGCTAGCAGACCGAAAACAG-3'.
```

The above primer pair is used to amplify the genome of the TaCAT gene of wheat materials with obvious resistance and sensitivity separation, such as JM1, YN805 and ZM082, the PCR amplification system is shown in Table 2, and the PCR amplification program is shown in Table 3.

TABLE 2

PCR amplification system of the primer TaCAT-F1 and the primer TaCAT-R1 to the TaCAT gene

| Component | Volume |
|---|---|
| 2 × Phanta Max buffer | 25 microliters (μL) |
| dNTP Mix(10 millimolar per liter abbreviated as mM each) | 1 μL |
| Template cDNA | 2 μL |
| Primers F/R (i.e., the forward primer and the reverse primer, 10 micromolar per liter abbreviated as μM) | 2/2 μL |
| Phanta Max Super-Fidelity DNA Polymerase | 1 μL |
| Double distilled water (dd $H_2O$) | 17 μL |

TABLE 3

PCR amplification program of the primer TaCAT-F1 and the primer TaCAT-R1 to the TaCAT gene

| — | Process | Temperature | Time |
|---|---|---|---|
| Step 1 | Pre-denaturation | 95 Celsius degree (° C.) | 5 minutes (min) |
| Step 2 | Denaturation | 95° C. | 30 seconds (s) |
| 34 cycles | Annealing | Melting temperature (Tm) | 30 s |
| | Extension | 72° C. | 2 min |
| Step 3 | Thorough extension | 72° C. | 10 min |
| Step 4 | Stored at 4° C. | — | — |

Figures 3A, 3B:
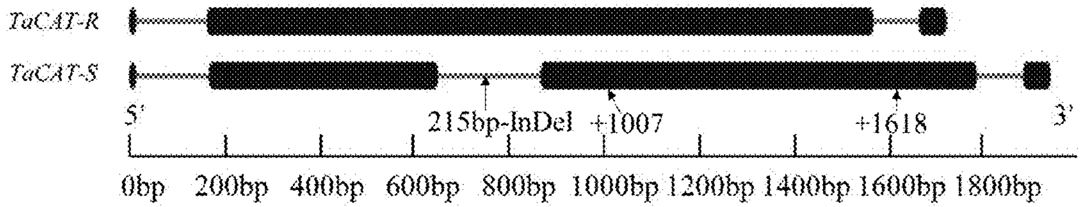
FIG. 3A illustrates a schematic structural diagram of a TaCAT gene in a resistant and susceptible material.
FIG. 3B illustrates a schematic diagram of an analysis of different haplotypes of the TaCAT gene.
Figure 3C:
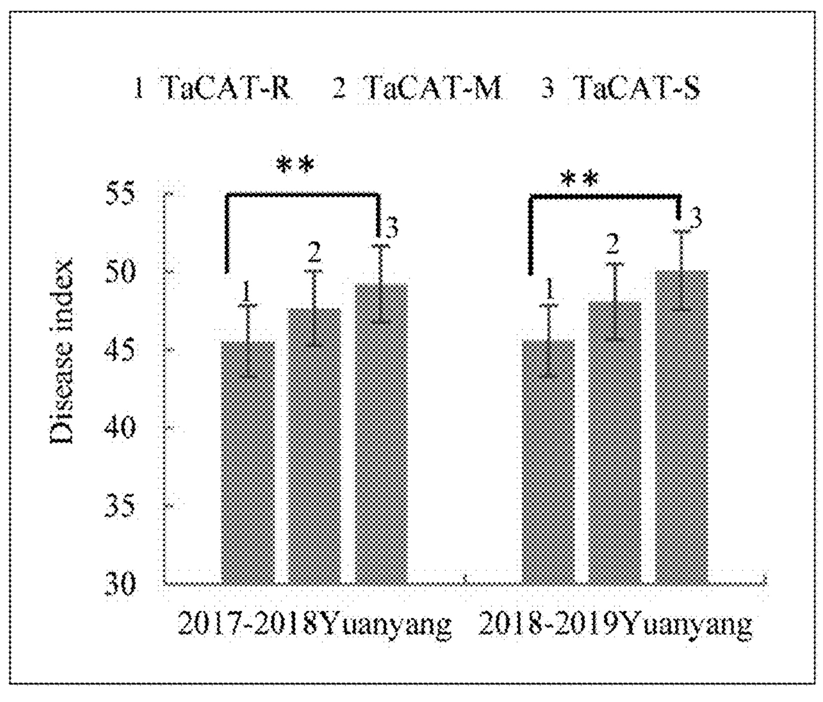
FIG. 3C illustrates a schematic diagram of corresponding phenotypes of the different haplotypes of the TaCAT gene.

It is discovered through sequencing analysis that the TaCAT gene of the susceptible material has an additional intron with 215 bp than that of the resistant material. Meanwhile, there are two amino acid site differences in the gene coding region, namely Thr214Ser and Arg418Lys (FIG. 3A). The sequencing analysis is further performed on the 243 wheat materials in the natural population to discover that the difference sites of the TaCAT gene in the resistant and susceptible materials are clearly separated, which forms a total of 8 haplotypes and 3 genotypes (FIG. 3B). Based on the phenotyping, it is found that the resistance differences among the three genotypes are significant (FIG. 3C), which indicates that the TaCAT gene is significantly related to the FCR of wheat.

Embodiment 2 Development and Application of an Allele Marker of the TaCAT Gene

According to the nucleotide sequence of the TaCAT gene as shown in SEQ ID NO: 1, there is an insertion or deletion of 215 bp between the resistant and susceptible materials staring from the 654$^{th}$ position after a start codon ATG. An InDel marker is developed according to the insertion or deletion fragment to detect different genotypes of the TaCAT gene. The differential site-specific primer pair includes: an upstream primer with the nucleotide sequence as shown in SEQ ID NO: 7:5'-CCCGATCTTGCTGGAGGA-3', and a downstream primer with the nucleotide sequence as shown in SEQ ID NO: 8: 5'-AAGACGCGCCAATACTCCTG-3'.

Figure 4A:
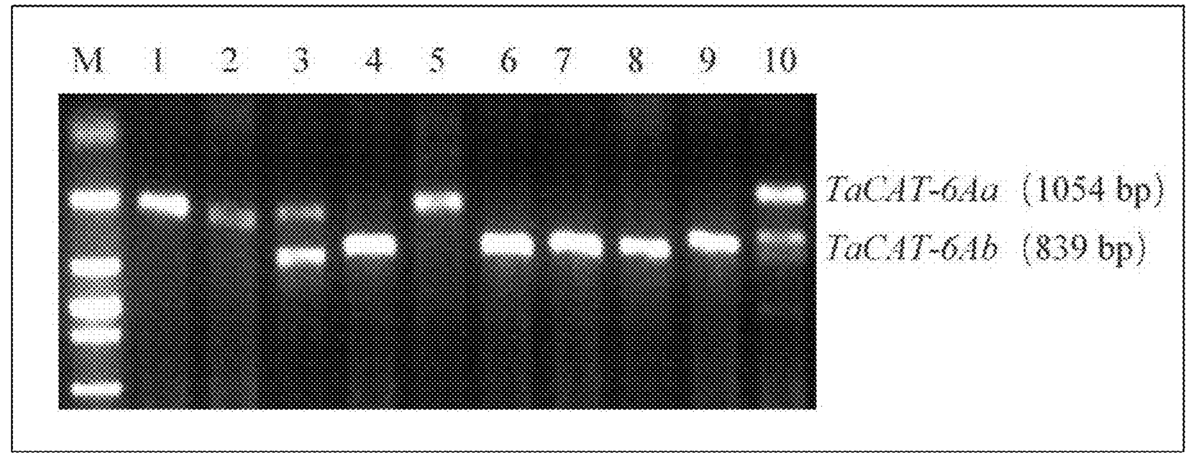
FIG. 4A illustrates a detecting schematic diagram of an InDel marker of the TaCAT gene in a part of families in a JY population.

The specific InDel marker is used to amplify DNA from different materials. A genotype of a wheat variety/strain with an amplification product of 1054 bp is named as TaCAT-6Aa, a genotype of a wheat variety/strain with an amplification product of 839 bp is named as TaCAT-6Ab (FIG. 4A), and there is a significant difference in the disease resistance ability of plants corresponding to the two genotypes.

Figure 4B:
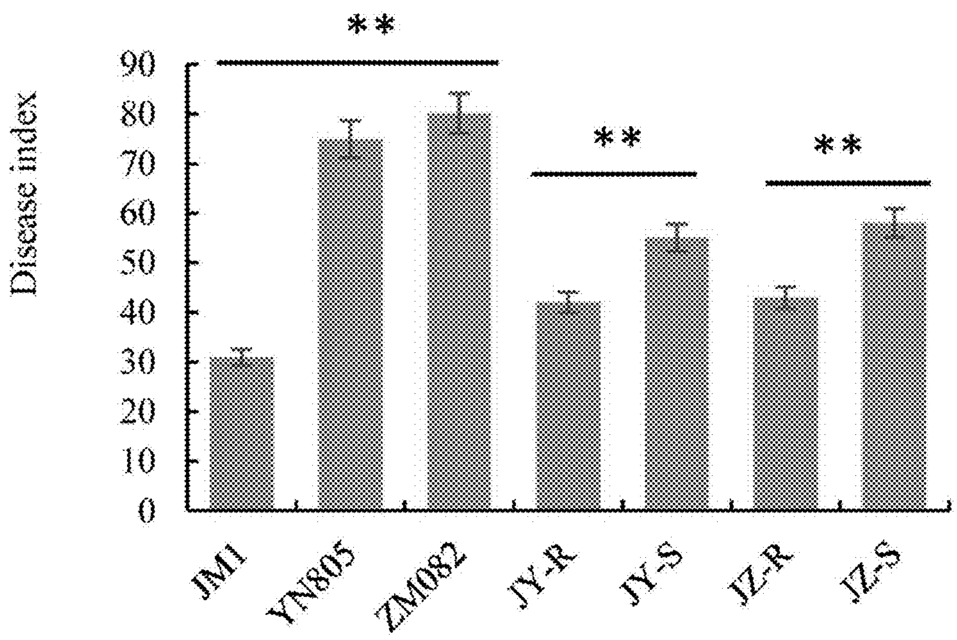
FIG. 4B illustrates a schematic diagram of a verification result of the InDel marker of the TaCAT gene in descendant populations.

The developed InDel marker of the TaCAT gene is further detected and verified in the JY and JZ populations to obtain results as shown in FIG. 4B, that is, the two alleles of TaCAT-6Aa and TaCAT-6Ab in the populations are clearly separated, and the corresponding resistance to the FCR of wheat is significantly different. This marker can be used as a detection marker and an auxiliary selection marker for disease-resistance for the TaCAT gene of the wheat.

Embodiment 3 VIGS Silencing and Phenotypic Identification of the TaCAT Gene (1) Construction of a VIGS Vector of the TaCAT Gene Primers are designed according to the cDNA sequence of the TaCAT gene, and a restriction enzyme cutting site and a protective base are added to the 5' ends of the forward and reverse primers, respectively, to form the upstream primer TaCAT-F2 as shown in SEQ ID NO: 9: 5'-AGCTAGCT-GATTAATTAAGCAACAACTTCCCCGTCTTC-3', and the downstream primer TaCAT-R2 as shown in SEQ ID NO: 10: 5'-TGCTAGCT-GAGCGGCCGCAAGAAGAAGGTGTGGAGGCT-3'. The VIGS fragment of the TaCAT gene is amplified by using the primer pair and recovered for later use. The γ-PDS vector is double-digested with PacI and NotI to obtain a γ-PDS linearized vector fragment. The recovered fragment and the γ-PDS linearized vector fragment are used to complete the construction of the recombinant vector (γ-TaCAT) by a seamless cloning method.

(2) Plant VIGS Experiment of the TaCAT Gene

The viral vector (α, β, γ, γ-PDS) and the TaCAT gene silencing recombinant vector (γ-TaCAT) plasmids are linearized by digestion, and the linearized plasmids are further transcribed in vitro by using a RiboMAX™ Large Scale RNA Production Systems-T7 kit to obtain different components of viral in vitro transcription products. 2.5 μL of each of the in vitro transcription products α, β, γ/γ-PDS/γ-TaCAT is taken, mixed with a ratio of 1:1:1, and diluted with an equal volume of diethyl pyrocarbonate (DEPC) water to obtain diluted mixture. 5 μL of the diluted mixture is taken and added to 90 μL of FES buffer solution to obtain a mixture, and the mixture is mixed thoroughly by pipetting to obtain a FES mixed solution. Four different treatments are set up for each experiment, including: a complete blank control group (WT), a virus blank control group (α+β+γ), an albino positive control group (α+β+γ-PDS) and a gene silencing group (α+β+γ-TaCAT).

Specifically, the FES buffer solution is obtained by the following steps: glycine is added with dipotassium hydrogenphosphate to obtain a mother liquid, and sodium pyrophosphate, bentonite and diatomaceous earth are added into the mother liquid to obtain the FES buffer solution.

When the virus is infected, a small amount of the DEPC water is sprayed on the surface of the plant to be infected (JM1). 10 μL of the FES mixed solution is applied on a clean glove, the second leaf of the seedling is rubbed from the base to the tip for three times with controlled strength by the glove, and a little DEPC water is sprayed from top to bottom to maintain humidity after rubbing. The glove need to be changed to a clean one for each treatment. After the virus is inoculated, it is placed in a 23±2° C. incubator to keep warm, moisturize and avoid light for 24 h, and then adjust it to a 16 h/8 h light and dark cycle for cultivation, and observe and record phenotypic changes regularly.

(3) Phenotypic Identification after VIGS for the TaCAT Gene

Figure 5:
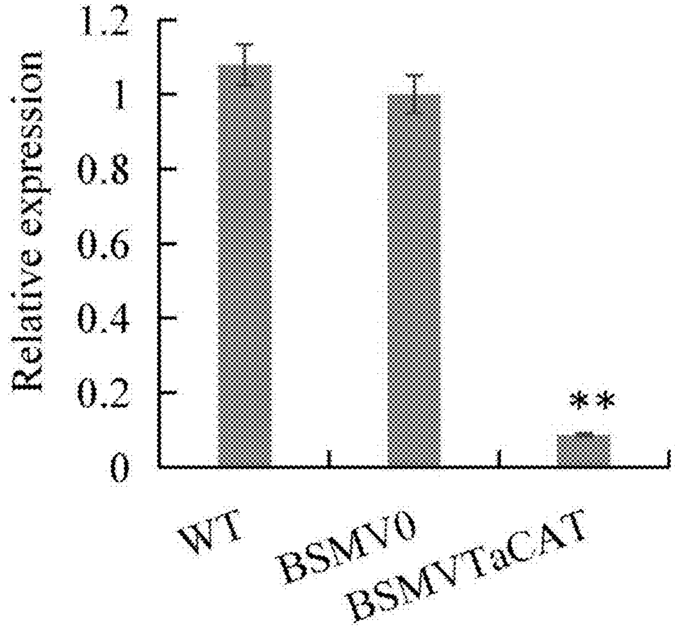
FIG. 5 illustrates a schematic diagram of a relative expression level of the TaCAT gene in a VIGS experiment.

After 2 weeks of VIGS for the TaCAT gene, the relative expression levels of the TaCAT gene in a silenced plant (BSMVTaCAT), a virus-free plant (BSMV0) and a non-silenced plant (WT) are detected by a qRT-PCR technology. The result shows that the relative expression level of the TaCAT gene in the silenced plant is significantly downregulated, and the gene is effectively silenced (FIG. 5).

Figure 6A:
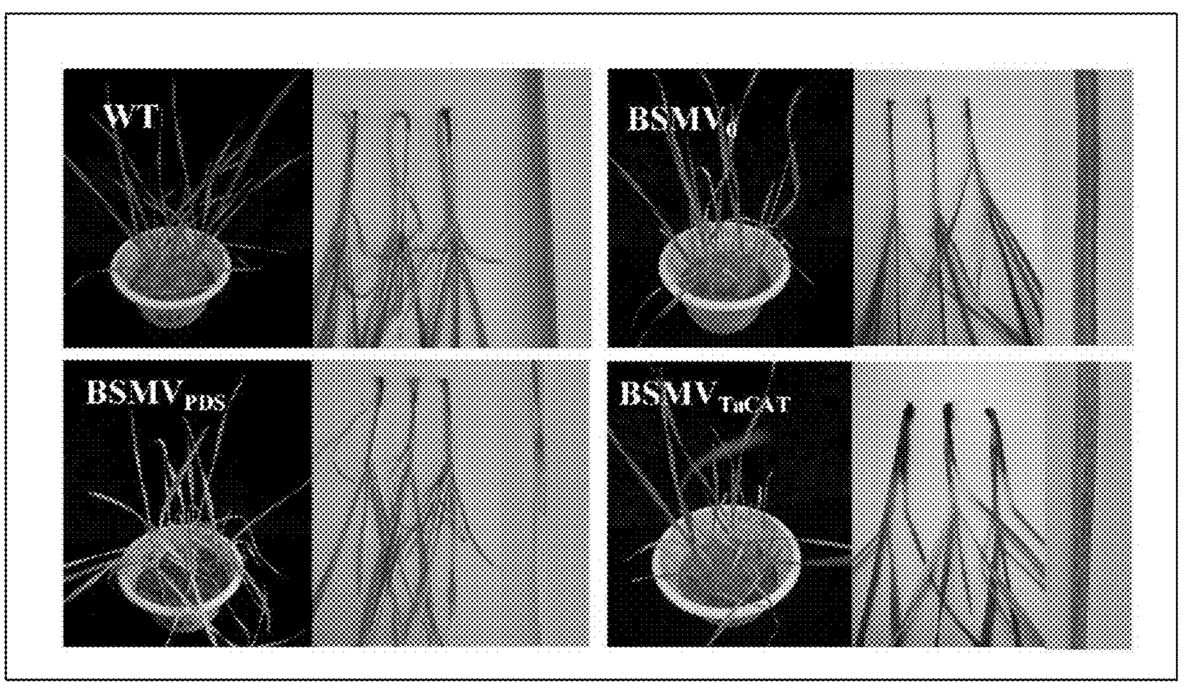
FIG. 6A illustrates a schematic diagram of effects of the TaCAT gene silenced by the VIGS of wheat treated with different materials.
Figure 6B:
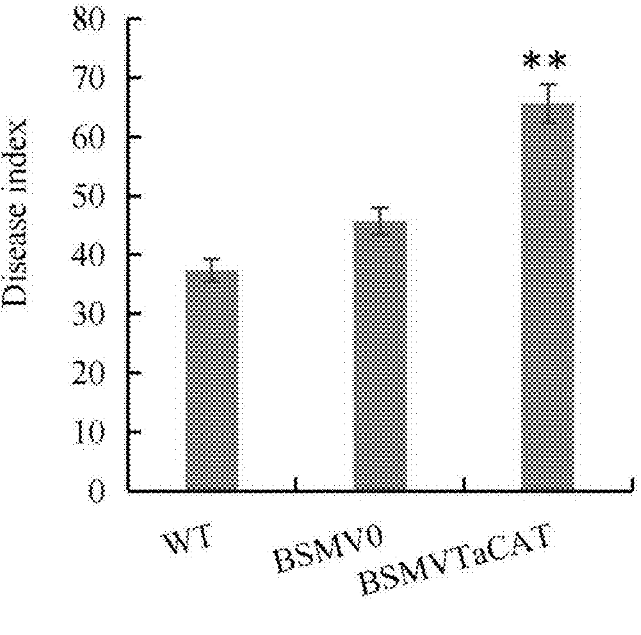
FIG. 6B illustrates a schematic diagram of disease indexes of wheat treated with different materials after silencing the TaCAT gene.
Figure 7A:
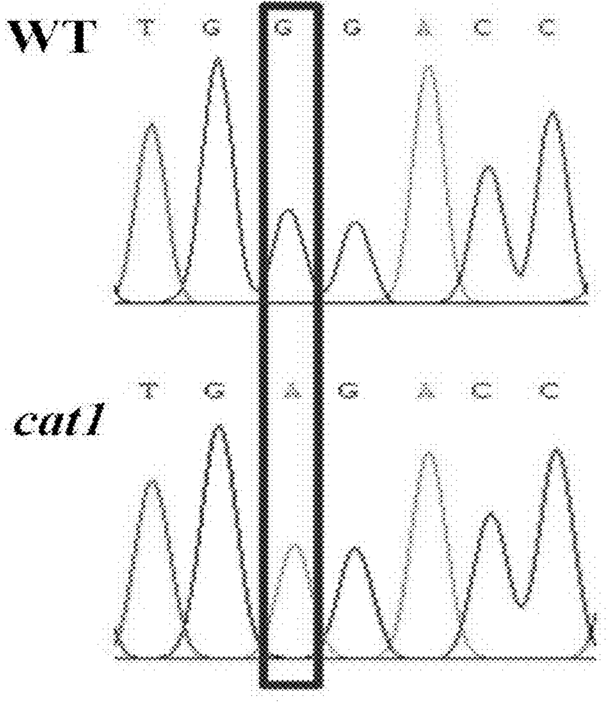
FIG. 7A illustrates a schematic diagram of a cat1 mutant site.
Figure 7B:
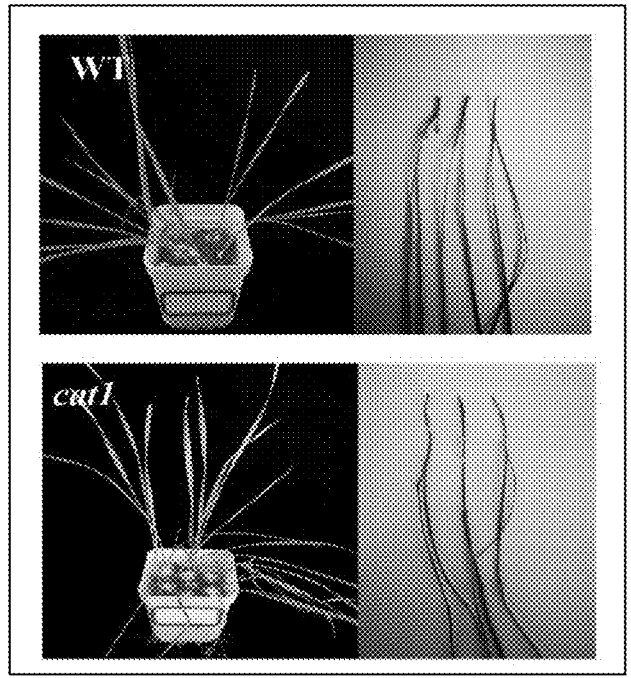
FIG. 7B illustrates a schematic comparative diagram of phenotypes of resistance to FCR of wheat of a Kronos3868 positive mutant (i.e., the cat1) and a wide-type Kronos in a seedling stage.
Figure 7C:
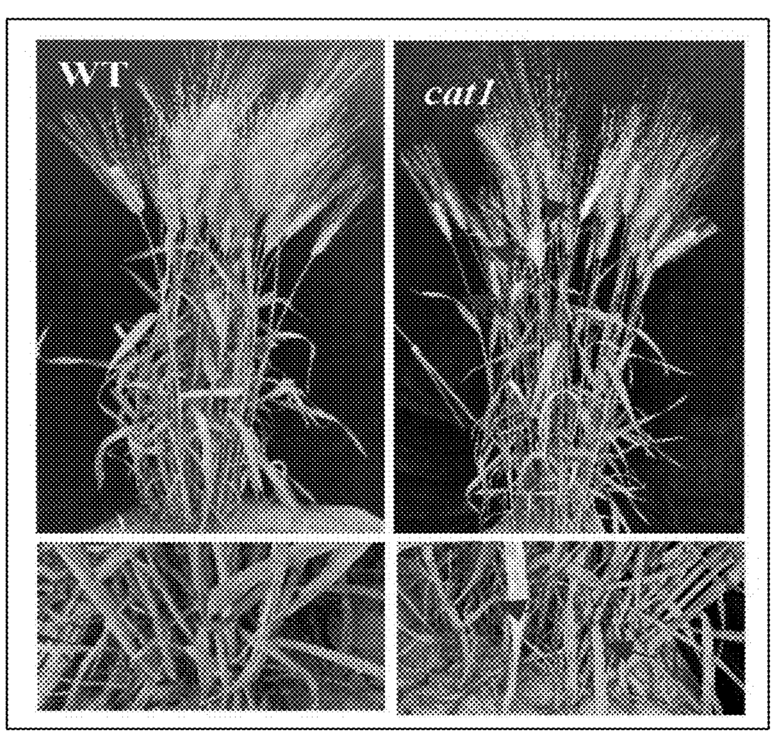
FIG. 7C illustrates a schematic comparative diagram of phenotypes of resistance to FCR of wheat of the cat1 and the wide-type Kronos in an adult plant stage.
Figure 7D:
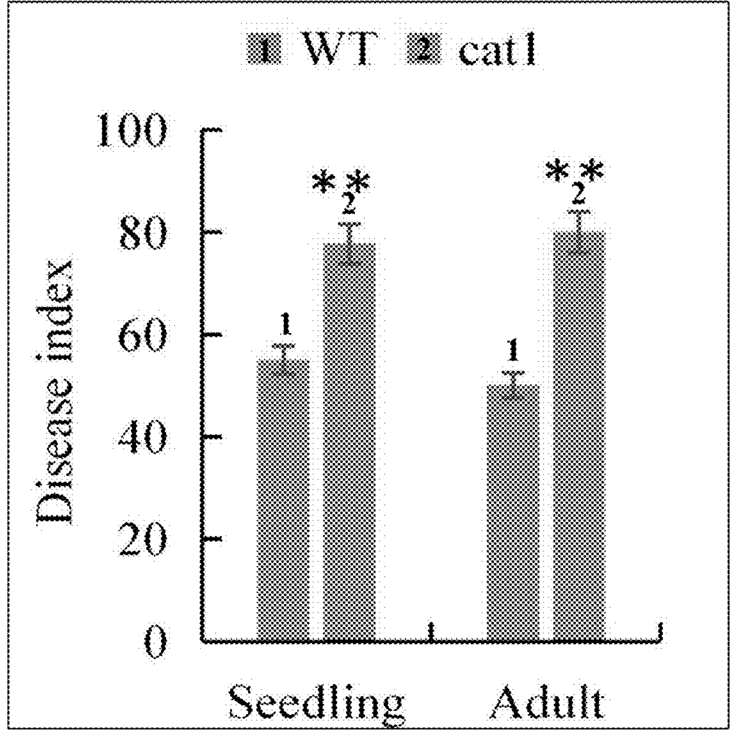
FIG. 7D illustrates a schematic comparative diagram of disease indexes of the cat1 and the wide-type Kronos in the seedling stage and the adult plant stage.

The phenotype of the silenced plant for the FCR is further identified, and the result shows that the disease index of the TaCAT gene-silenced plant (disease index abbreviated as DI=67.90) is significantly higher than that of the virus-free plant (JM1, DI=37.66), and the disease-resistance of the plants is significantly reduced (FIGS. 6A and 6B).

In summary, the disease-resistance of plants with silenced TaCAT gene is significantly reduced, which indicates that the TaCAT gene is a gene that positively regulates resistance to the FCR of wheat.

Embodiment 4 Verification of an Ethyl Methane Sulfonate (EMS) Mutant of the TaCAT Gene The disease-resistance of the TaCAT gene is further verified by using a tetraploid mutant induced by EMS. Kronos3868 is a premature termination mutant of the TaCAT gene, and the nucleotide at $396^{th}$ bp after the 5' end ATG of the TaCAT gene sequence mutates from G to A, causing the gene to terminate prematurely. After backcrossing the Kronos3868 positive mutant with the wild-type Kronos-WT twice to eliminate the background difference of the materials, the resistance of the backcrossed Kronos3868 (named cat1) and the wild-type Kronos-WT materials to the FCR of wheat is further identified at the seedling and adult plant stages.

The result shows that the disease indexes corresponding to cat1 ($DI_{seedling\ stage}$=77.78, $DI_{adult\ plant\ stage}$=80) are significantly higher than that of Kronos-WT ($DI_{seedling\ stage}$=55, $DI_{adult\ plant\ stage}$=50) whether the plant is in the seedling stage or the adult plant stage, and the disease-resistance of the plants is significantly reduced (FIGS. 7A-7D). It is speculated that the TaCAT gene plays a positive role in regulating the resistance to FCR of wheat in the plant.

Embodiment 5 Acquisition and Identification of a TaCAT Transgenic Wheat (1) Construction of a TaCAT Plant Overexpression Vector Primers are designed based on the full-length cDNA sequence of the TaCAT gene in Chinese spring (also refers to *Triticum aestivum*, with a genome sequence of IWGSC RefSeq v2.1), and recognition sites and protective bases of restriction endonucleases BamHI and SacI are introduced at both ends of the primers. The primer sequences are as follows:

TaCAT-F3 as shown in SEQ ID NO: 11: 5'-GATGAC-GATGACAAGGGATCC-GATCCCTGCAAGTTCCGGC-3' (bases with the underlined are the recognition sites and protection bases of the restriction endonuclease BamHI); and TaCAT-R3 as shown in SEQ ID NO: 12: 5'-ACGAACGAAAGCTCTGAGCTCTCA-CATGCTTGGCTTCACG-3' (bases with the underlined are the recognition sites and protection bases of the restriction endonuclease SacI).

A TRIzol reagent is used to extract total RNA from the seedling stage of JM1. The RNA is used as a template, and a SuperScript III reverse transcriptase (Invitrogen, Cat NO: 18080-044) is used for reverse transcription to obtain cDNA. The cDNA is used as a template, and the PCR amplification is performed on a coding sequence of the TaCAT gene of the wheat by using the primers TaCAT-F3 and TaCAT-R3. The amplification product is recovered and purified for later use.

Figure 8:
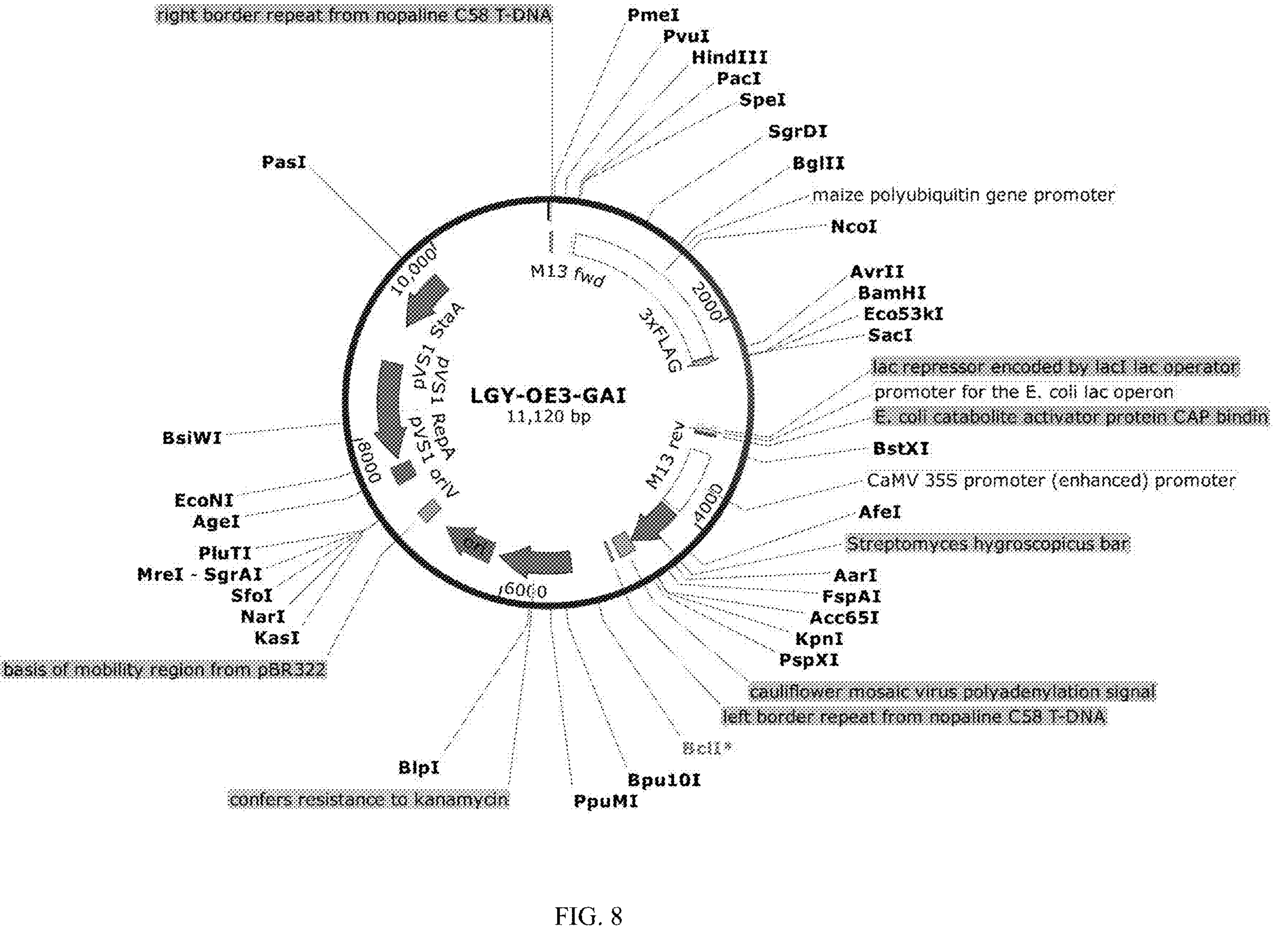
FIG. 8 illustrates a schematic diagram of a graph of an overexpression vector pLGY-OE3.

The plant expression vector pLGY-OE3 is selected, and its vector map is shown in FIG. 8.

The plant expression vector is double-digested with BamHI and SacI, recovered and purified to obtain a purified plant expression vector, and the recombinant vector (pLGY-OE3-TaCAT) is constructed by the purified plant expression vector with the above DNA fragment.

(2) Acquisition of the TaCAT Transgenic Wheat

Immature embryo callus of wheat KN199 is transformed by using the pLGY-OE3-TaCAT and an *Agrobacterium* infection method, and positive plants are obtained after screening, pre-differentiation and differentiation. The PCR amplification is performed on the positive plants by using primers TaCAT-F4 and TaCAT-R4 to obtain amplification products, and the amplification products are sequenced to obtain $T_0$ generation transgenic plants.

The sequences of the primers include:

```
TaCAT-F4 as shown in SEQ ID NO: 13:
5'-ATTCATATGCTCTAACCTTGAGT-3';
and

TaCAT-R4 as shown in SEQ ID NO: 14:
5'-TGGGCGATCTTCTCCAGCAG-3'.
```

The PCR amplification system is shown in Table 4, and the PCR amplification program is shown in Table 5.

TABLE 4

PCR amplification system of the primers TaCAT-F4 and TaCAT-R4 for the TaCAT gene

| Component | Volume |
|---|---|
| 5 × Mix Enzyme | 5 μL |
| TaCAT-F4 | 0.5 μL |
| TaCAT-R4 | 0.5 μL |
| DNA | 1 μL |
| dd $H_2O$ | To 10 μL |

TABLE 5

PCR amplification program of the primers TaCAT-F4 and TaCAT-R4 for the TaCAT gene

| — | Process | Temperature | Time |
|---|---|---|---|
| Step 1 | Pre-denaturation | 95° C. | 5 min |
| Step 2 | Denaturation | 95° C. | 30 s |
| 34 cycles | Annealing | Tm | 30 s |
| | Extension | 72° C. | 40 s |
| Step 3 | Thorough extension | 72° C. | 10 min |
| Step 4 | Stored at 4° C. | — | — |

(3) PCR Identification and Phenotypic Identification of the Transgenic Wheat

The PCR amplification is performed on overexpression plants by using the primers TaCAT-F4 and TaCAT-R4 to obtain amplification products, and the amplification products are sequenced to screen positive transgenic plants, and a total of 10 positive transgenic lines are obtained. After additional generations, a $T_2$ generation transgenic line is obtained.

The primers TaCAT-F5 and TaCAT-R5 are used for fluorescence real-time quantitative PCR for detecting the expression level of the TaCAT gene in the leaves of the $T_2$ generation positive transgenic plants.

The sequences of the primers include:

```
TaCAT-F5 as shown in SEQ ID NO: 15:
5'-ACACCTACACCTTCGTCTCC-3;
```

-continued

```
and

TaCAT-R5 as shown in SEQ ID NO: 16:
5'-GCACGAACAGCTTCCACTC-3'.
```

The PCR amplification system is shown in Table 6, and the PCR amplification program is shown in Table 7.

TABLE 4

PCR amplification system of the primers TaCAT-F5 and TaCAT-R5 for the TaCAT gene

| Component | Volume |
|---|---|
| 2 × SYBR Premix | 5 μL |
| Forward Primer (TaCAT-F5) | 0.5 μL |
| Reverse Primer (TaCAT-R5) | 0.5 μL |
| cDNA | 2 μL |
| Nuclease-Free Water | 2 μL |

TABLE 7

PCR amplification program of the primers TaCAT-F5 and TaCAT-R5 for the TaCAT gene

| Temperature | Time | Cycles |
|---|---|---|
| 95° C. | 30 s | 1 |
| 95° C. | 10 s | 45 |
| 60° C. | 20 s | 45 |
| 72° C. | 20 s | 45 |

Figure 9:
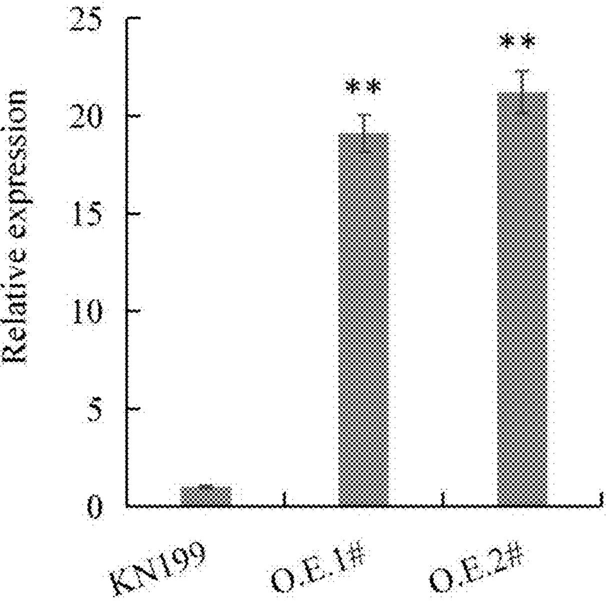
FIG. 9 illustrates a schematic diagram of relative expression levels of transgenic lines (TaCAT-OX1 and TaCAT-OX2) with TaCAT gene overexpression.

The result is shown in FIG. 9. The expression level of the target TaCAT gene in the leaves of the $T_2$ generation positive transgenic plants is significantly higher than that of the wild-type KN199, and is about 18 to 22 times the expression level in the empty leaves.

The overexpression transgenic lines $T_2$ (TaCAT-OX1 (i.e. O.E.1 #), TaCAT-OX2 (i.e. O.E.2 #)) and wild-type KN199 are further identified for resistance to the FCR at the seedling and adult plant stages. The identification results are shown in FIG. 10.

Figure 10A:
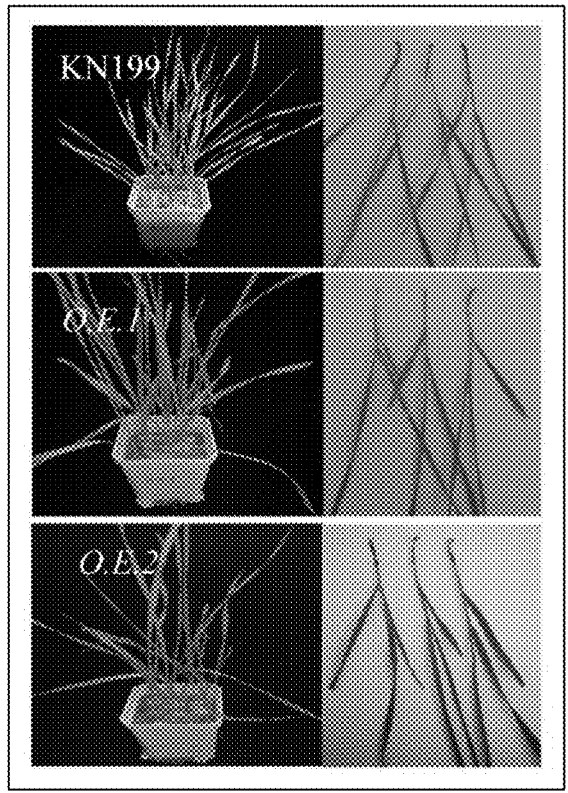
FIG. 10A illustrates a schematic comparative diagram of phenotypes of resistance to FCR of wheat of the transgenic lines (TaCAT-OX1 and TaCAT-OX2) with TaCAT gene overexpression and a wide-type KN199 in the seedling stage.
Figure 10B:
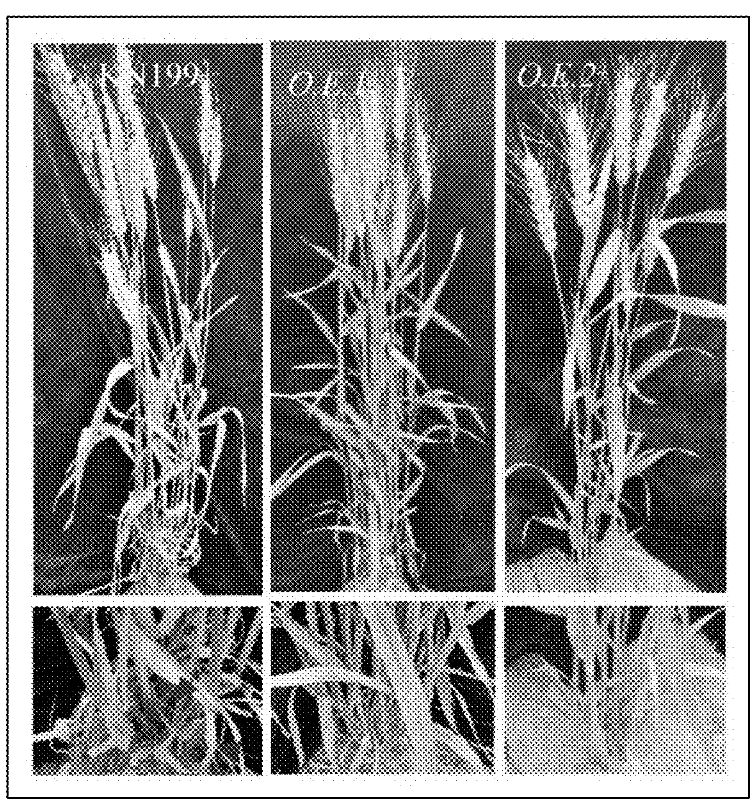
FIG. 10B illustrates a schematic comparative diagram of phenotypes of resistance to FCR of wheat of the transgenic lines (TaCAT-OX1 and TaCAT-OX2) with TaCAT gene overexpression and the wide-type KN199 in the adult plant stage.
Figure 10C:
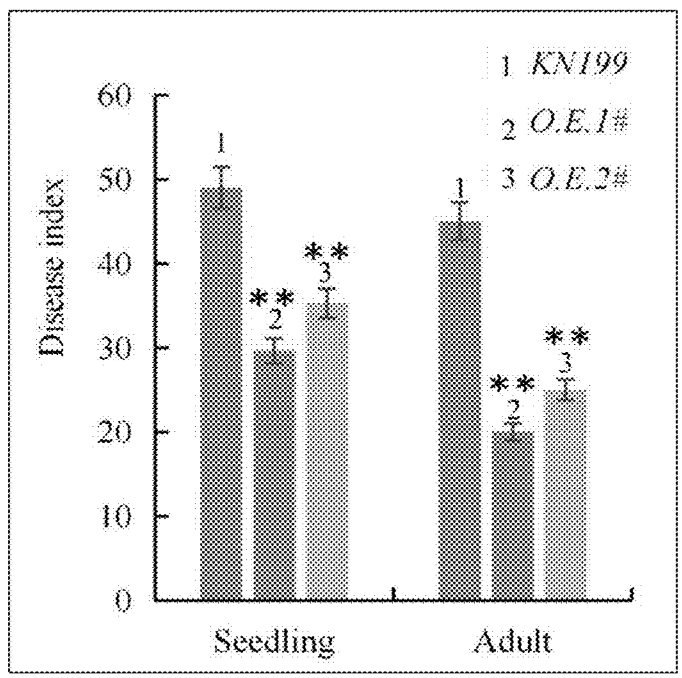
FIG. 10C illustrates a schematic comparative diagram of disease indexes of the transgenic lines (TaCAT-OX1 and TaCAT-OX2) with TaCAT gene overexpression and the wide-type KN199 in the seedling stage and the adult plant stage.

Compared with the wild-type KN199 plants, the disease indexes of the overexpressing transgenic lines $T_2$ (TaCAT-OX1 andTaCAT-OX2) to the FCR is significantly reduced, and the disease-resistance of the plants is significantly improved (FIGS. 10A-10C).

In summary, the TaCAT gene related to the FCR of wheat of the disclosure can regulate resistance to the FCR of wheat, can be further used to study the molecular mechanism related to controlling the FCR of wheat, and has important application value in wheat disease-resistance breeding.

The embodiments described above are merely some of the embodiments of the disclosure, and are not intended to limit the scope of implementation of the disclosure. Therefore, any equivalent changes or amendments made according to the structures, features and principles described in the patent scope of the disclosure should be included in the scope of the disclosure.

What is claimed is:

1. A method for detecting an allelotype with resistance or susceptibility to *Fusarium* crown rot in wheat, comprising:

extracting genomic DNA of a to-be-detected wheat;

taking the genomic DNA of the to-be-detected wheat as a template, performing a polymerase chain reaction (PCR) amplification with an upstream primer with the nucleotide sequence as shown in SEQ ID NO: 5, and a downstream primer with the nucleotide sequence as shown in SEQ ID NO: 6 to obtain an amplification product, comparing a gene sequence of the amplification product with the gene sequence as shown in SEQ ID NO: 1 to obtain a comparison result, and determining an allelotype of the to-be-detected wheat based on the comparison result; wherein the determining an allelotype of the to-be-detected wheat based on the comparison result comprises:

in response to 215 base pairs (bp) in the gene sequence of the amplification product being missing starting from a 654th position after a start codon adenine-thymine-guanine (ATG) compared to the gene sequence as shown in SEQ ID NO: 1, determining that the to-be-detected wheat is a deletion type; and in response to the gene sequence of the amplification product being the same as the nucleotide sequence as shown in SEQ ID NO: 1, determining that the to-be-detected wheat is an insertion type;

determining that the to-be-detected wheat is resistant to *Fusarium* crown rot when the allelotype of the to-be-detected wheat is determined to be the deletion type; and breeding a wheat variety resistant to *Fusarium* crown rot by using the to-be-detected wheat determined to be resistant.

2. A method for detecting an allelotype with resistance or susceptibility to *Fusarium* crown rot in wheat, comprising:

extracting genomic DNA of a to-be-detected wheat;

taking the genomic DNA of the to-be-detected wheat as a template, performing a PCR amplification with an upstream primer with the nucleotide sequence as shown in SEQ ID NO: 7, and a downstream primer with the nucleotide sequence as shown in SEQ ID NO: 8, to obtain the amplification product, and determining an allelotype of the to-be-detected wheat based on the amplification product; wherein the determining an allelotype of the to-be-detected wheat based on the amplification product comprises:

in response to a size of the amplification product being 1054 bp, determining that the to-be-detected wheat is an insertion type; and in response to a size of the amplification product being 839 bp, determining that the to-be-detected wheat is a deletion type;

determining that the to-be-detected wheat is resistant to *Fusarium* crown rot when the allelotype of the to-be-detected wheat is determined to be the deletion type; and breeding a wheat variety resistant to *Fusarium* crown rot by using the to-be-detected wheat determined to be resistant.

* * * * *

SEQUENCE LISTING

```
Sequence total quantity: 16
SEQ ID NO: 1           moltype = DNA  length = 2470
FEATURE                Location/Qualifiers
source                 1..2470
                       mol_type = other DNA
```

```
                         organism = Triticum aestivum
SEQUENCE: 1
aagaccggct cgagcgagct caggcagagc agagagcagt gcagtgagag tgagtgagct  60
cgccacactc cccccagctt agcggagcta cctcactcaa gagaggaagg atggatccct  120
gcaaggtaag cagacacgat cagactaatc ctatgctact ttacagtcca tggtgttctt  180
aattcgttca catagattct accgattata gtacgtgtgt gcgtgtgctg attaattaac  240
atcgagctct gtgtgcgtgc gtgtgcatgg cgtgcagttc cggccgtcga gcagcttcga  300
caccaagacg acgacgacca acgccgggca gccggtgtgg aacgacaacg aggcgctcac  360
cgtcggcccg cgcggcccga tcttgctgga ggactaccac ctgctggaga agatcgccca  420
cttcgcgcgc gagcgcatcc cggagcgggt ggtgcacgcg cggggcgcct ccgccaaggg  480
cttcttcgag tgcacccacg acgtgacggg cttgacctgc gccgacttcc tccgcgcgcc  540
gggggcgcgc acgccggtca tcgtccgctt ttccacggtg atccacgagc gcggctcgcc  600
ggagacgatc cgtgacccgc gcgggttcgc cgtcaagttc tacacgcgcg agggcaactg  660
ggacctgctc ggcaacaact tccccgtctt cttcatccgc gacggcatca agttccccga  720
cgtcatccat gccttcaagc ccaacccaaa gtcccacgtg caggcaaggt tttatttatt  780
tatttcggaa acaagataat ttctagcctc atccaaatat gcaaattttc gaaaatgaat  840
tctagcataa cttaaattta ttttaaaacc agttaatttg aatcttccgt gaaatttcag  900
ggttaaaaat gttcctgacc tcactgaaat atactaaatt ttggaaattt ctttggattt  960
ttttaacctt gtgtgcagga gtattggcgc gtcttcgact tcctttccca ccacccggag  1020
agcctccaca ccttcttctt cctcttcgac gacgtcggca tcccgaccga ctaccgccac  1080
atggacggct tcggcgtcaa cacctacacc ttcgtcaccc gcgccggcaa gtcccactac  1140
gtcaagttcc actggaggcc cacctgcggc gtcagctgcc tcatggacga cgaggccacg  1200
ctcgtcggcg gcaagaacca cagccacgcc acccaggacc tctacgactc catcgacgcc  1260
ggcaacttcc ccgagtggaa gctgttcgtg caggtcatcg accccgacga cgaggaccgc  1320
ttcgacttcg acccgctcga cgacaccaag acatggcccg aggacctcgt ccccctccag  1380
cccgtcggcc gcctcgtgct cgaccgcaac gtcgacaact tcttcaacga gaacgagcag  1440
ctggccttcg gcccggggct cgtcgtgcct gggatctact actccgacga caagatgctg  1500
cagtgcaggg tgttcgccta cgccgacacg cagcgctacc gcctcggccc aaactacctg  1560
atgctccccg tcaacgcgcc caagtgcggc ttcaagaaca accactacga cggcgccatg  1620
aacttcatgc accgcgacga ggaggtggac tactacccgt cccgccacgc gccgctccgg  1680
caggcggagc cggccagctt ccctgtgccc acgcggcccg tcgtcggaag aagggagaag  1740
acgaggatca agaaggagaa cgacttcgtg cagcccgggg agaggtaccg cagctgggcg  1800
cccgaccgcc aggacaggtt cgtgcgccgc ttcgccgacg ccctcgccca ccccaaggtc  1860
agccacgagc tccgcgtcat ctggatcgac ttcctctcca aggtaactaa ttgttgatgc  1920
atgaacccat ggatgtacgc tcaatgttct tcagttggtg atgaatgatt aactcggttg  1980
atttgtggat ggatgcagtg tgacaagtcg tgcggcatga aggtggcgaa ccgtctcaac  2040
gtgaagccaa gcatgtgatg gatggaccgt tctgtgtaaa ctttgtgcta tatcatggac  2100
cagcaataag agaccatgcc agctataatg tggatcatgt ggtcgattac ctactgtgct  2160
gctactaata agttactatc attttctttt atgtcgcagt aacttacctg taatccagca  2220
aatgaaatta aagtgggtgc tttggagctt atgaatccaa acgtgtattc gtctttgcct  2280
cagatgatat ttgctgttct ggatggaaca agatggctct gttttcggtc tgctagccac  2340
atcaaagttt gttttgcacg accttctgtg acaactttga gtaacaaaga gcggaaatta  2400
gaaagtgcac ccgctccctg cccccaaaga acaattcccc aatgtaaaaa gatactacat  2460
cgatccgtct                                                         2470

SEQ ID NO: 2             moltype = DNA  length = 1845
FEATURE                  Location/Qualifiers
source                   1..1845
                         mol_type = genomic DNA
                         organism = Triticum aestivum
SEQUENCE: 2
agagagcagt gcagtgagag tgagtgagct cgccacactc cccccagctt agcggagcta  60
cctcactcaa gagaggaagg atggatccct gcaagttccg gccgtcgagc agcttcgaca  120
ccaagacgac gacgaccaac gccgggcagc cggtgtggaa cgacaacgag gcgctcaccg  180
tcggcccgcg cggcccgatc ttgctggagg actaccacct gctggagaag atcgcccact  240
tcgcgcgcga gcgcatcccg gagcgggtgg tgcacgcgcg gggcgcctcc gccaagggct  300
tcttcgagtg cacccacgac gtgacgggct tgacctgcgc cgacttcctc cgcgcgccgg  360
gggcgcgcac gccggtcatc gtccgctttt ccacggtgat ccacgagcgc ggctcgccgg  420
agacgatccg tgacccgcgc gggttcgccg tcaagttcta cacgcgcgag ggcaactggg  480
acctgctcgg caacaacttc cccgtcttct tcatccgcga cggcatcaag ttccccgacg  540
tcatccatgc cttcaagccc aacccaaagt cccacgtgca ggagtattgg cgcgtcttcg  600
acttcctttc ccaccacccg gagagcctcc acaccttctt cttcctcttc gacgacgtcg  660
gcatcccgac cgactaccgc cacatggacg gcttcggcgt caacacctac accttcgtca  720
cccgcgccgg caagtcccac tacgtcaagt tccactggag gcccacctgc ggcgtcagct  780
gcctcatgga cgacgaggcc acgctcgtcg gcggcaagaa ccacagccac gccacccagg  840
acctctacga ctccatcgac gccggcaact tccccgagtg gaagctgttc gtgcaggtca  900
tcgaccccga cgacgaggac cgcttcgact tcgacccgct cgacgacacc aagacatggc  960
ccgaggacct cgtccccctc cagcccgtcg gccgcctcgt gctcgaccgc aacgtcgaca  1020
acttcttcaa cgagaacgag cagctggcct tcggcccggg gctcgtcgtg cctgggatct  1080
actactccga cgacaagatg ctgcagtgca gggtgttcgc ctacgccgac acgcagcgct  1140
accgcctcgg cccaaactac ctgatgctcc ccgtcaacgc gcccaagtgc ggcttcaaga  1200
acaaccacta cgacggcgcc atgaacttca tgcaccgcga cgaggaggtg gactactacc  1260
cgtcccgcca cgcgccgctc cggcaggcgg agccggccag cttccctgtg cccacgcggc  1320
ccgtcgtcgg aagaagggag aagacgagga tcaagaagga gaacgacttc gtgcagcccg  1380
gggagaggta ccgcagctgg gcgcccgacc gccaggacag gttcgtgcgc cgcttcgccg  1440
acgccctcgc ccaccccaag gtcagccacg agctccgcgt catctggatc gacttcctct  1500
ccaagtgtga caagtcgtgc ggcatgaagg tggcgaaccg tctcaacgtg aagccaagca  1560
tgtgatggat ggaccgttct gtgtaaactt tgtgctatat catggaccag caataagaga  1620
ccatgccagc tataatgtgg atcatgtggt cgattaccta ctgtgctgct actaataagt  1680
```

-continued

```
tactatcatt ttcttttatg tcgcagtaac ttacctgtaa tccagcaaat gaaattaaag  1740
tgggtgcttt ggagcttatg aatccaaacg tgtattcgtc tttgcctcag atgatatttg  1800
ctgttctgga tggaacaaga tggctctgtt ttcggtctgc tagcc                  1845

SEQ ID NO: 3           moltype = DNA  length = 1485
FEATURE                Location/Qualifiers
source                 1..1485
                       mol_type = genomic DNA
                       organism = Triticum aestivum
SEQUENCE: 3
atggatccct gcaagttccg gccgtcgagc agcttcgaca ccaagacgac gacgaccaac  60
gccgggcagc cggtgtggaa cgacaacgag gcgctcaccg tcggcccgcg cggcccgatc  120
ttgctggagg actaccacct gctggagaag atcgcccact tcgcgcgcga gcgcatcccg  180
gagcgggtgg tgcacgcgcg gggcgcctcc gccaagggct tcttcgagtg cacccacgac  240
gtgacgggct tgacctgcgc cgacttcctc cgcgcgccgg gggcgcgcac gccggtcatc  300
gtccgctttt ccacggtgat ccacgagcgc ggctcgccgg agacgatccg tgacccgcgc  360
gggttcgccg tcaagttcta cacgcgcgag ggcaactggg acctgctcgg caacaacttc  420
cccgtcttct tcatccgcga cggcatcaag ttccccgacg tcatccatgc cttcaagccc  480
aacccaaagt cccacgtgca ggagtattgg cgcgtcttcg acttcctttc ccaccacccg  540
gagagcctcc acaccttctt cttcctcttc gacgacgtcg gcatcccgac cgactaccgc  600
cacatggacg gcttcggcgt caacacctac accttcgtca cccgcgccgg caagtcccac  660
tacgtcaagt tccactggag gcccacctgc ggcgtcagct gcctcatgga cgacgaggcc  720
acgctcgtcg gcggcaagaa ccacagccac gccacccagg acctctacga ctccatcgac  780
gccggcaact tccccgagtg gaagctgttc gtgcaggtca tcgaccccga cgacgaggac  840
cgcttcgact tcgacccgct cgacgacacc aagacatggc ccgaggacct cgtccccctc  900
cagcccgtcg gccgcctcgt gctcgaccgc aacgtcgaca acttcttcaa cgagaacgag  960
cagctggcct tcggcccggg gctcgtcgtg cctgggatct actactccga cgacaagatg  1020
ctgcagtgca gggtgttcgc ctacgccgac acgcagcgct accgcctcgg cccaaactac  1080
ctgatgctcc ccgtcaacgc gcccaagtgc ggcttcaaga acaaccacta cgacggcgcc  1140
atgaacttca tgcaccgcga cgaggaggtg gactactacc cgtcccgcca cgcgccgctc  1200
cggcaggcgg agccggccag cttccctgtg cccacgcggc ccgtcgtcgg aagaagggag  1260
aagacgagga tcaagaagga gaacgacttc gtgcagcccg gggagaggta ccgcagctgg  1320
gcgcccgacc gccaggacag gttcgtgcgc cgcttcgccg acgccctcgc ccaccccaag  1380
gtcagccacg agctccgcgt catctggatc gacttcctct ccaagtgtga caagtcgtgc  1440
ggcatgaagg tggcgaaccg tctcaacgtg aagccaagca tgtga                  1485

SEQ ID NO: 4           moltype = AA  length = 494
FEATURE                Location/Qualifiers
source                 1..494
                       mol_type = protein
                       organism = Triticum aestivum
SEQUENCE: 4
MDPCKFRPSS SFDTKTTTTN AGQPVWNDNE ALTVGPRGPI LLEDYHLLEK IAHFARERIP  60
ERVVHARGAS AKGFFECTHD VTGLTCADFL RAPGARTPVI VRFSTVIHER GSPETIRDPR  120
GFAVKFYTRE GNWDLLGNNF PVFFIRDGIK FPDVIHAFKP NPKSHVQEYW RVFDFLSHHP  180
ESLHTFFFLF DDVGIPTDYR HMDGFGVNTY TFVSRAGKSH YVKFHWRPTC GVSCLMDDEA  240
TLVGGKNHSH ATQDLYDSID AGNFPEWKLF VQVIDPDDED RFDFDPLDDT KTWPEDLVPL  300
QPVGRLVLDR NVDNFFNENE QLAFGPGLVV PGIYYSDDKM LQCRVFAYAD TQRYRLGPNY  360
LMLPVNAPKC GFKNNHYDGA MNFMHRDEEV DYYPSRHAPL RQAEPASFPV PTRPVVGKRE  420
KTRIKKENDF VQPGERYRSW APDRQDRFVR RFADALAHPK VSHELRVIWI DFLSKCDKSC  480
GMKVANRLNV KPSM                                                    494

SEQ ID NO: 5           moltype = DNA  length = 20
FEATURE                Location/Qualifiers
source                 1..20
                       mol_type = other DNA
                       organism = Triticum aestivum
SEQUENCE: 5
agagagcagt gcagtgagag                                              20

SEQ ID NO: 6           moltype = DNA  length = 20
FEATURE                Location/Qualifiers
source                 1..20
                       mol_type = other DNA
                       organism = synthetic construct
SEQUENCE: 6
ggctagcaga ccgaaaacag                                              20

SEQ ID NO: 7           moltype = DNA  length = 18
FEATURE                Location/Qualifiers
source                 1..18
                       mol_type = other DNA
                       organism = synthetic construct
SEQUENCE: 7
cccgatcttg ctggagga                                                18

SEQ ID NO: 8           moltype = DNA  length = 20
FEATURE                Location/Qualifiers
source                 1..20
```

```
                        mol_type = other DNA
                        organism = synthetic construct
SEQUENCE: 8
aagacgcgcc aatactcctg                                20

SEQ ID NO: 9            moltype = DNA  length = 38
FEATURE                 Location/Qualifiers
source                  1..38
                        mol_type = other DNA
                        organism = synthetic construct
SEQUENCE: 9
agctagctga ttaattaagc aacaacttcc ccgtcttc            38

SEQ ID NO: 10           moltype = DNA  length = 38
FEATURE                 Location/Qualifiers
source                  1..38
                        mol_type = other DNA
                        organism = synthetic construct
SEQUENCE: 10
tgctagctga gcggccgcaa gaagaaggtg tggaggct            38

SEQ ID NO: 11           moltype = DNA  length = 40
FEATURE                 Location/Qualifiers
source                  1..40
                        mol_type = other DNA
                        organism = synthetic construct
SEQUENCE: 11
gatgacgatg acaagggatc cgatccctgc aagttccggc          40

SEQ ID NO: 12           moltype = DNA  length = 40
FEATURE                 Location/Qualifiers
source                  1..40
                        mol_type = other DNA
                        organism = synthetic construct
SEQUENCE: 12
acgaacgaaa gctctgagct ctcacatgct tggcttcacg          40

SEQ ID NO: 13           moltype = DNA  length = 23
FEATURE                 Location/Qualifiers
source                  1..23
                        mol_type = other DNA
                        organism = synthetic construct
SEQUENCE: 13
attcatatgc tctaaccttg agt                            23

SEQ ID NO: 14           moltype = DNA  length = 20
FEATURE                 Location/Qualifiers
source                  1..20
                        mol_type = other DNA
                        organism = synthetic construct
SEQUENCE: 14
tgggcgatct tctccagcag                                20

SEQ ID NO: 15           moltype = DNA  length = 20
FEATURE                 Location/Qualifiers
source                  1..20
                        mol_type = other DNA
                        organism = synthetic construct
SEQUENCE: 15
acacctacac cttcgtctcc                                20

SEQ ID NO: 16           moltype = RNA  length = 19
FEATURE                 Location/Qualifiers
source                  1..19
                        mol_type = other RNA
                        organism = synthetic construct
SEQUENCE: 16
gcacgaacag cttccactc                                 19
```